United States Patent [19]
Fujii et al.

[11] 3,979,457
[45] Sept. 7, 1976

[54] PROCESS FOR PRODUCTION OF (+)-2-AMINO-1-BUTANOL

[75] Inventors: Chiyuki Fujii; Moroshi Yasui; Yoshiaki Ishimathu, all of Machida, Japan

[73] Assignee: Denki Kagaku Kogyo Kabushiki Kaisha, Tokyo, Japan

[22] Filed: Sept. 30, 1974

[21] Appl. No.: 510,194

[30] Foreign Application Priority Data

Sept. 28, 1973  Japan.............................. 48-108975

[52] U.S. Cl. ........................ 260/584 R; 260/482 R; 260/534 R
[51] Int. Cl.² ................... C07C 89/00; C07C 91/02
[58] Field of Search ......... 260/584 R, 534 R, 482 R

[56] References Cited
UNITED STATES PATENTS

| | | | |
|---|---|---|---|
| 3,116,332 | 12/1963 | Sullivan............................ | 260/584 R |
| 3,553,257 | 1/1971 | Halmos....................... | 260/584 R X |
| 3,579,586 | 5/1971 | Zola................................. | 260/584 R |
| 3,579,587 | 5/1971 | Zola................................. | 260/584 R |
| 3,769,347 | 10/1973 | Kazan ............................ | 260/584 R |

OTHER PUBLICATIONS

Birnbaum et al., Journal of Biol. Chem., V194 pp. 455–470 (1952).
J.A.C.S. vol. 76, 2801–2803 (1954).
J.A.C.S. vol. 83, pp. 2212–2213 (1961).
Chemical Abstracts, vol. 79, 65780e (1973).

*Primary Examiner*—Helen M. S. Sneed
*Attorney, Agent, or Firm*—Sughrue, Rothwell, Mion, Zinn & Macpeak

[57] ABSTRACT

A process for producing (+)-2-amino-1-butanol comprising optically resolving an N-acyl-DL-aminobutyric acid using an acylase to obtain L-2-aminobutyric acid and an N-acyl-D-aminobutyric acid which is recycled after racemization, esterifying the L-2-aminobutyric acid to form L-2-aminobutyric acid ester, and reducing the L-2-aminobutyric acid ester to form (+)-2-amino-1-butanol.

13 Claims, No Drawings

PROCESS FOR PRODUCTION OF (+)-2-AMINO-1-BUTANOL

BACKGROUND OF THE INVENTION

1. Field of the Invention

The present invention relates to a process for the production of (+)-2-amino-1-butanol. More particularly, the present invention relates to a process for producing (+)-2-amino-1-butanol which comprises esterifying L-2-aminobutyric acid obtained by the optical resolution of DL-2-aminobutyric acid and reducing the resulting L-2-aminobutyric acid ester.

2. Description of the Prior Art (+)-2-Amino-1-butanol is an important intermediate for producing (+)-2,2'-(ethylenediimino)di-1-butanol (generally called Ethambutol) which has a remarkable antitubercular action, and only the (±)-2-amino-1-butanol is required (see Wilkinson R. G. et al, J. Am. Chem. Soc. 83, 2212 (1961)).

Also, it is known that racemic form or meso form -(ethylenediimino)di--(ethylenediimino) 1-butanol produces strong undesirable side effects on the eyes (see, for example, Arch. Ophtal. 67, 566 (1962) and Ibid, 68, 718 (1962)). Thus, an extremely high optical purity is required for (+)-2-amino-1-butanol.

Hitherto, (+)-2-amino-1-butanol has been produced by forming an intermediate of 2-nitrobutanol from 1-nitropropane as a starting material, synthesizing (±)-2-amino-1-butanol from the intermediate, and optically resolving the (±)-2-amino-1-butanol. The yields obtained have averaged as low as about 10%. Furthermore, (−)-2-aminobutanol simultaneously produced is quite difficult to be racemized and thus the hitherto used method is economically disadvantageous.

In the course of investigations on a process for producing (+)-2-amino-1-butanol which is different from the hitherto used method, attention was directed toward the optical isomers produced by the optical resolution of DL-2-aminobutyric acid and in detail toward a reducing method and reducing agent for the ester of the DL-2-aminobutyric acid. As a result, it has been found that (+)-2-amino-1-butanol can be produced from L-2-aminobutyric acid and an economical synthesis of (+)-2-amino-1-butanol has been established.

SUMMARY OF THE INVENTION

An object of the present invention is to provide a process for producing (+)-2-amino-1-butanol.

The present invention provides a process for producing (+)-2-amino-1-butanol which comprises optically resolving an N-acyl-DL-aminobutyric acid using an acylase to form L-2-aminobutyric acid and an N-acyl-D-aminobutyric acid which is recycled after racemization, esterifying the L-2-aminobutyric acid to form L-2-aminobutyric acid ester, and reducing the L-2-aminobutyric acid ester to form (+)-2-amino-1-butanol.

DETAILED DESCRIPTION OF THE INVENTION

The present invention comprises the combination of the step of optically resolving an N-acyl-DL-2-aminobutyric acid to form L-2-aminobutyric acid and an N-acyl-D-aminobutyric acid which is recycled after racemization and the step of esterifying the L-2-aminobutyric acid followed by the reduction of the resulting L-2-aminobutyric acid ester.

In the first step, N-acyl-DL-2-aminobutyric acid is optically resolved to obtain L-2-aminobutyric acid. In general, as methods for resolving N-acyl-DL-2-aminobutyric acid to obtain the L-form thereof, various methods such as a crystallization method, an adsorption method, a chemical method, an enzyme method, and the like have been proposed.

It is known that the enzyme resolution method using the action of an aminoacylase (hereinafter referred to as "acylase" for brevity) is effective in obtaining L-amino acid of high purity in high yields. However, an acylase has a substrate specificity depending upon the amino acid acted upon and thus an acylase has been used only in producing several kinds of L-amino acids such as L-methionine, L-phenylalanine, and the like.

Investigation of the optical resolution of N-acyl-DL-2-aminobutyric acid using an acylase has revealed that L-2-aminobutyric acid of high purity can be obtained in high yields.

One reason why this fact has not been discovered before now can be explained as follows. Although it might be relatively easily considered that DL-2-aminobutyric acid, $CH_3CH_2CH(NH_2)COOH$, is suitable as a starting material for use in producing 2-amino-1-butanol, $CH_3CH_2CH(NH_2)CH_2OH$, the resolution of the N-acyl-DL-2-aminobutyric acid has not been of commercial interest. Thus, in accordance with the hitherto used method, DL-2-aminobutanol has been resolved and the purity required has been attained only by controlling the yield.

In accordance with the method of the present invention, DL-2-aminobutyric acid is resolved, esterified, and reduced, and thus the advantage of the present invention is that 2-amino-1-butanol of the same purity as in the hitherto used method, e.g., as disclosed in British Pat. No. 961,317 can be obtained in yields of 80% or more.

DL-2-aminobutyric acid as used in the present invention is a 2-amino acid which can be easily obtained by general synthetic methods for producing a 2-amino acid.

Examples of these methods can be schematically illustrated as follows for the production of a 2-aminobutyric acid.

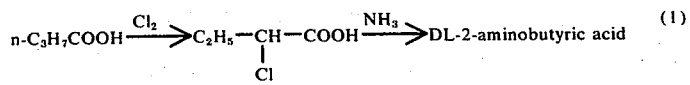

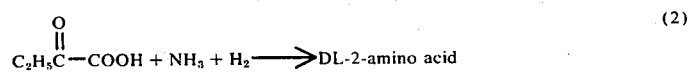

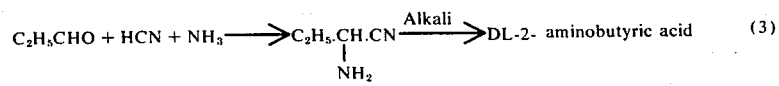

DL-2-aminobutyric acid can be easily acylated with various acylating agents using conventional methods to form an acetyl derivative, a formyl derivative, a benzoyl derivative, and the like thereof. Of these derivatives, the acetyl derivative and the chloroacetyl derivative are most suitably subject to the action of an acylase.

The acylase which can be used in the present invention is commercially available and either acylase I derived from the kidney of pigs or an acylase derived from fungi can be used in the resolution of DL-2-aminobutyric acid. These acylases are described in Barman, Enzyme Handbook, Volume II, Springer-Verlag Publisher (New York), 1969, page 656 (Enzyme Commission Number 3.5.1.14); and "Studies on Amino Acids V – VIII" by Chibata, Watanabe and Yamada in Bull. Agr. Chem. Soc. Japan, Vol. 21, No. 5, pages 291–307, 1957. In this latter article, fungal acylases are referred to as "mold acylases." Fungal acylase obtained from a species of genus Aspergillus is made by Amano Seiyaku K.K. (Japan) and Acylase I is manufactured by Nakarai Kagaku K.K. (Japan).

The acylase can be used either in a soluble enzyme form wherein the acylase is dissolved in water or in an immobilized enzyme form wherein acylase is rendered insoluble in water. Particularly, the use of the immobilized enzyme form is advantageous in that the amount of enzyme to be added can be markedly reduced.

Various methods for using acylase in the water insoluble form are known and a typical method is to ionically adsorb an acylase onto a polysaccharide based anion exchange resin such as DEAE-Sephadex (a trademark manufactured by Pharmacia Fine Chemical Co., Ltd.), DEAE-cellulose, and the like. A most suitable method comprises immobilizing an acylase on an anion exchange resin containing pyridine rings in the resin which are quaternized as described in Japanese Pat. Laid Open Application No. 49-19082 (Feb. 20, 1974) as an effective enzyme immobilizing carrier.

The anion exchange resin having quaternized pyridine rings in the resin as used as a carrier is a reactive polymer which is insoluble in water but is highly hydrophilic, and which is produced by copolymerizing vinyl pyridine or a derivative thereof and one or more monomers copolymerizable therewith selected from the group consisting of an aromatic vinyl compound, an ethylenically unsaturated compound and a diene compound, and reacting the copolymer with an agent to quaternize the nitrogen atom of the pyridine ring.

More specifically, anion exchange resins having quaternized pyridine rings which are suitable are produced by reacting a vinyl pyridine-styrene-divinyl benzene copolymer, a vinyl pyridine-methyl methacrylate-divinyl benzene copolymer, a vinyl pyridine-polyethylene glycol dimethacrylate copolymer, a vinyl pyridine-styrene block copolymer, a vinyl pyridine-methyl methacrylate block copolymer, or the like with an agent such as an alkyl halide, an alkyl dihalide and the like where the alkyl moiety contains 1 to 4 carbon atoms and the halogen is chlorine, fluorine or iodine. Preferred resins are those resins having an ion exchange capacity of about 2.0 to 5.0 millimole equivalent/g and a degree of swelling of about 2.0 to 50.0 ml/g (in a 0.1 M phosphoric acid buffer solution at a pH of 8.0).

The optical resolution of DL-2-aminobutyric acid using the action of a commercially available acylase, particularly an acylase derived from filamentous fungi which is fixed to an anion exchange resin having quaternized pyridine rings in the resin has been investigated and as a result, it has been found that the enzyme activity of the acylase to DL-2-aminobutyric acid is quite high, and thus a continuous enzyme reaction using a column reactor is made possible for a long period of time and a novel process has been established which is advantageous from an industrial standpoint as well as from an economical standpoint.

The optical resolution of N-acyl-DL-2-aminobutyric acid using an acylase is carried out under the conditions which are most suitable for the substrate of the acylase. For instance, in optically resolving N-acetyl-DL-2-aminobutyric acid using a fungal acylase, if the temperature is controlled to about 30° to 70°C, preferably 37° to 40°C, the pH is adjusted to about 5 to 8.5, preferably 7 to 8, the concentration of the substrate is controlled to about 0.05 to 1 mol/l and the acylase is dissolved in water in an amount of about 40 to 4,000, preferably 500 to 2,000, units, per gram of the substrate and is used, the optical resolution proceeds to 100% completion within about 100, preferably 24 hours, and L-2-aminobutyric acid having an optical purity of 99% or more can be obtained. On the other hand, when an immobilized acylase prepared by adsorbing about 0.5 to 5 parts of a fungal acylase in case of 10,000 units per g) onto 1 part of an anion exchange resin having quaternized pyridine rings in the resin is charged in a column maintained at an internal temperature of about 30° to 70°C, preferably 50°C, and a solution of a concentration of about 0.05 to 1 mole of N-acetyl-DL-2-aminobutyric acid in water (pH of about 5 to 8.5, preferably 7.0 to 8) is fed in the column at a rate of about 0.5 to 10, preferably 1 to 10, parts per hour, no significant reduction of enzyme activity is observed even after the passage of about 500 hours and L-2-aminobutyric acid can be obtained at a conversion of about 100%. A suitable space velocity ranges from about 0.5 to 10 $hr^{-1}$.

In accordance with the latter method, i.e., continuous method, the amount of the enzyme used can be reduced to about one-tenth to one-twentieth that used in the former method, and thus the latter method is quite economical.

In addition, the advantage of the latter method is that when the enzyme activity is reduced by the removal of acylase adsorbed during the long continued reaction, acylase can be fed into the column in an amount corresponding to that removed to compensate for the removal and the reaction can be again carried out at high conversions.

The solution obtained from the optical resolution comprises predominantly L-2-aminobutyric acid with a small amount of an N-acyl-D-2-aminobutyric acid (A) or predominantly an N-acyl-D-2-aminobutyric acid with a small amount of L-2-aminobutyric acid (B). The L-2-aminobutyric acid and the N-acyl-D-2-aminobutyric acid contained is Solution (A) or Solution (B) can be separated from each other using general procedures such as a crystallization, and adsorption, a chemical method, an extraction, an enzymatic method and the like. Particularly preferred procedures for this separation include a method comprising adding a solvent which selectively crystallizes only the L-2-aminobutyric acid in the solution to obtain crystalline L-2-aminobutyric acid and a method comprising contacting the solution with a strongly acidic ion exchange resin to selectively adsorb the L-2-aminobutyric acid and eluting the desired acid with an appropriate eluent such as hydrochloric acid, aqueous ammonia, aqueous sodium hydroxide and the like.

The N-acyl-D-2-aminobutyric acid simultaneously produced in the optical resolution of the first stage can be racemized and subjected to the optical resolution method herein described, if desired.

The racemization of the N-acyl-D-aminobutyric acid followed by the optical resolution can be accomplished by heating the N-acyl-D-aminobutyric acid. In this procedure, it was found that the absence of water markedly accelerates the racemization. Otherwise, a high temperature and a long period of time are required for completion of the reaction thereby resulting in the formation of undesirable by-products due to the decomposition of the N-acyl-D-aminobutyric acid. Further, the presence of water also causes a racemization of the L-2-aminobutyric acid which remains unseparated during the isolation step as described above. Thus, when the water content of the system of N-acyl-D-aminobutyric acid is less than about 1% by weight, preferably less than 0.5%, selective racemization of the N-acyl-D-aminobutyric acid can be carried out at a temperature which does not cause the racemization of L-2-aminobutyric acid without forming a substantial amount of by-products. The reaction can be carried out by heat-melting the crystalline N-acyl-D-aminobutyric acid which contains a small amount of L-2-aminobutyric acid or dissolving or dispersing the crystals in an inert solvent followed by heating at a temperature of from about 110° to 170°C for a period of about 5 minutes to 24 hours, preferably 30 minutes to 3 hours. In one embodiment, the N-acyl-D-aminobutyric acid can be heated in the presence of an inert solvent which is capable of forming an azeotropic mixture with water thereby effectively distilling off the water to selectively racemize N-acyl-D-aminobutyric acid. Suitable inert solvents which can be used in the racemization include those having a boiling point of about 50° to 180°C, e.g., hydrocarbons, for example, saturated aliphatic or alicyclic hydrocarbons or aromatic hydrocarbons, ethers, such as straight chain ethers or cyclic ethers, nitriles such as alkyl mono- or di-nitriles, carboxylic acids, esters such as alkylacetates and the like.

The thus obtained L-2-aminobutyric acid can be esterified and converted into (+)-2-amino-1-butanol of high purity without racemization occurring.

It is known that a 2-amino-acid ester can be converted to a 2-amino-alcohol using hydrogenation agents such as $LiAlH_4$, $NaBH_4$, and the like, and alkali metals as used in the Bouveault-Blanc reduction, but these metals are difficult to use industrially since they are expensive. Also, a 2-amino-acid ester can be converted into a 2-amino-alcohol using a catalytic reduction in which Raney-nickel, copper chromium oxide, rhenium oxide, and the like are employed. However, catalytic reductions using copper chromium oxide, rhenium oxide, and the like as a catalyst generally require severe conditions (high temperature and high pressure) and thus various side reactions and considerable racemization result.

In the catalytic reduction in which Raney nickel is used as a catalyst, the same severe conditions as with copper chromium oxide are required if the Raney nickel is used in the amount generally used as a catalyst, and thus side reactions and racemization cannot be avoided. When Raney nickel is used in a large amount, the reduction is known to proceed at temperatures of 100°C or less.

However, in this case, a hydrogen pressure of 150 atmospheres or more is required and thus generally various side reactions such as elimination of an amino group, alkylation, excessive reduction, cyclization, and the like occur.

In reducing L-2-aminobutyric acid and taking the above into account, it has now been found that the reduction proceeds at low temperatures of 70°C or less and at a hydrogen pressure of atmospheric pressure to a pressure of 70 atmospheres, preferably a pressure of 30 atmospheres or less without side reactions and racemization occurring by adding a large amount of Raney nickel to the 2-amino-acid ester, resulting in the formation of (+)-2-amino-1-butanol of high optical purity in high yields. That is, when Raney nickel is used in amounts of about 50% by weight or more, preferably 100% by weight or more, based upon the weight of the 2-amino-acid ester, or platinum is used in amounts of about 10% by weight or more, preferably 30% by weight or more, based upon the weight of the 2amino-acid ester, the 2-amino-acid ester is reduced under mild conditions of temperatures of about 70°C or less and hydrogen pressure of about 10 atmospheres or less and thus (+)-2-amino-1-butanol can be produced without causing side reactions and racemization. The upper limit of the amount of the above catalyst is not critical, and is appropriately determined from economic considerations. Although the amount of the catalyst herein used is very large, the catalyst can be repeatedly reused, and therefore, the cost involved is not a consideration. On the other hand, when the amount of the reducing catalyst is slightly reduced, for example, the Raney nickel is used in an amount of about 50% by weight of the 2-amino-acid ester, or platinum is used in an amount of about 10% by weight of the 2amino-acid ester, the reduction can be carried out by increasing the hydrogen pressure to on order of 30 to 70 Kg/cm² even at a temperature of 70°C or less. Even in this case, side reactions and racemization are hardly observed. However, if the amount of the reducing catalyst is decreased below the above level, severe conditions are required and side reaction and racemization remarkedly occur making the amount unsuitable for the present invention.

Suitable solvents which can be used in the catalytic reduction are any solvents which are non-reactive to the 2-amino-acid ester. Examples of solvents are aliphatic alcohols, tetrahydrofuran, dioxane, and the like. Use of the same alcohol as that forming the 2-amino-acid ester as the solvent is particularly preferred.

The ester moiety of the L-2-aminobutyric acid ester which are not affected by the subsequent reduction are preferred. Thus, alkyl esters formed by aliphatic alcohols such as methanol, ethanol, iso-propanol, 2-ethylhexanol, and the like are preferred.

The esterification of L-2-aminobutyric acid proceeds substantially quantitatively by reacting the L-2-aminobutyric acid with the alcohol at room temperature (about 20°–30°C) up to the boiling point of the alcohol in the presence of an esterification catalyst without any racemization.

After the reduction is completed, the catalyst used is filtered. The filtrate is distilled under atmospheric pressure or under vacuum, and (+)-2-amino-1-butanol having an optical purity of about 100% is obtained in high yields.

In this way, in accordance with the present invention, the separation of acylase from the fungi is not necessary and thus the difficulties of this separation can be eliminated. An advantage of the present invention is that DL-2-aminobutyric acid is selected as a starting material. Furthermore, the optical resolution by the action of the acylase according to the present invention proceeds to about 100% completion and the amount of acylase employed can be about one-tenth to one-twentieth of the generally used enzyme amounts, which is quite advantageous from an economic standpoint.

It has been found that L-2-aminobutyric acid can be obtained from an N-acyl-DL-2-aminobutyric acid in high yields using the action of the acylase adsorbed on an anion exchange resin, and that (+)-2-amino-1-butanol can be produced by esterifying and reducing the L-2-aminobutyric acid as described above.

Furthermore, it has been found that (+)-2-amino-1-butanol can be obtained while preventing side reactions and racemization by reducing the 2-amino-acid ester produced by esterifying L-2-aminobutyric acid, at room temperatures to about 70°C and under hydrogen pressure of 70kg/cm$^2$ or less in the presence of Raney Nickel of about 50% by weight or more to the 2-amino-acid ester or platinum of about 10% by weight or more to the 2-amino-acid ester.

The present invention is explained in greater detail by reference to the following examples. Unless otherwise indicated, all parts, percents, ratios and the like are by weight.

Preparation of L-2-Aminobutyric Acid

EXAMPLE 1

14.5g of N-acetyl-DL-2-aminobutyric acid was dissolved in 1 liter of water and the pH thereof was adjusted to 7.5 with LiOH. To the solution was added 87,000 units of acylase I derived from the kidney of pigs and reacted at 37°C. When the L-2-aminobutyric acid produced was followed by a colorimetric determination using ninhydrin, it was found that about 100% conversion was attained in 17 hours. After the reaction was completed, 1 g of activated carbon was added and the acylase I was removed by filtration. The filtrate was passed through a column of an ion exchange resin Dowex 50-X8 (trade name) to adsorb the L-2-aminobutyric acid thereon and N-acetyl-D-2-aminobutyric acid was separated. The L-2-aminobutyric acid adsorbed on the column was eluted with 2 N NH$_4$OH and then water was removed under reduced pressure, and thus 4.2 g of L-2-aminobutyric acid was obtained.

The conversion was 81.5% assuming that the theoretical amount of L-2-aminobutyric acid was 5.15 g and the m.p. (decomposition) was 272° to 273°C.

| Elemental Analysis: | C | H | N |
|---|---|---|---|
| Calculated (%) | 46.6 | 8.8 | 13.6 |
| Found (%) | 46.7 | 8.7 | 13.7 |

-continued

| Elemental Analysis: | C | H | N |
|---|---|---|---|

$(\alpha)_D^{33} = +18.5° \pm 0.8°$ (C = 6.225, 6N HCl)

The optical purity was 99.2% on the basis of the value:
$(\alpha)_D^{19} = +18.65°$ (C=4.8, 6N HCl) which is described in Merck Index (7th Edition).

On the other hand, the liquid which was not adsorbed on the ion exchange resin was combined and substantially all of the water was removed under reduced pressure. Thereafter, the unreacted N-acetyl-D-2-aminobutyric acid was extracted with ethyl acetate. After removing the ethyl acetate and a small amount of acetic acid, 5.7 g of N-acetyl-D-2-aminobutyric acid was obtained.

The yield was 78.6% assuming that the theoretical amount of N-acetyl-D-2-aminobutyric acid was 7.25 g and the m.p. was 132.4°C.
$(\alpha)_D^{31} = +40.2° \pm 0.1°$ (C=10.5, H$_2$O)

EXAMPLE 2

14.5 g of N-acetyl-DL-2-aminobutyric acid was dissolved in 1 liter of water and the pH thereof was adjusted to 8.0 with LiOH. To the solution were added 83 mg of CoCl$_2$.2H$_2$O and 21,750 units of a fungal acylase and reacted at 37°C. When the L-2-aminobutyric acid produced was followed by a colorimetric determination using ninhydrin, it was found that about 100% conversion was attained in 17 hours. After the reaction was completed, 5 g of activated carbon was added and the acylase was removed by filtration. The filtrate was, in the same manner as described in Example 1, passed through the column of an ion exchange resin Dowex 50-X8 to adsorb the L-2-aminobutyric acid thereon and N-acetyl-D-2-aminobutyric acid was separated. The L-2-aminobutyric acid adsorbed on the column was eluted with 2N NH$_4$OH and water of the eluate was removed under reduced pressure, and thus 4.0 g of L-2-aminobutyric acid was obtained.

The yield was 77.7% assuming that the theoretical amount of L-2-aminobutyric acid was 5.15 g.
$(\alpha)_D^{31} = +18.4° \pm 0.5°$ (C=10.3, 5N HCl)

The optical purity was 98.7% on the basis of the value:
$(\alpha)_D^{19} = +18.65°$(C=4.8, 6N HCl) as described in Merck Index (7th Edition).

EXAMPLE 3

Preparation of Anion Exchange Resin (Carrier)

A monomer mixture of 24 mole % of styrene, 75 mole % of 2-vinyl pyridine and 1 mole % of divinyl benzene was suspension polymerized in the presence of benzoyl peroxide as a radical catalyst and the thus obtained polymer was quaternized with methyl bromide. One part of the quaternized styrene/2-vinyl pyridine/divinyl pyridine random copolymer (anion exchange capacity: 4.2 millimole equivalent/g) was placed in 50 parts of 0.1 M phosphoric acid buffer solution having a pH of 8.0 for 24 hours and separated by filtration, and thus a wet carrier was obtained.

Adsorption of Acylase on the Carrier (Prepaation of Immobilized Enzyme)

One part of the wet carrier as prepared above was added with stirring at room temperature to an enzyme solution prepared by dissolving 0.5 parts of a commercially available acylase (activity of about 10,000 units/g) in 50 parts of a 0.1 M phosphoric acid buffer solution (pH=8.0). After about 3 hours, the wet carrier was filtered, washed several times with water and then freeze-dried. The enzyme activity for N-acetyl-DL-2-aminobutyric acid was about 2,000 units/g.

Continuous Resolution of N-Acetyl-DL-2-aminobutyric Acid (Continuous Production of L-2-aminobutyric Acid)

1 g of the immobilized enzyme (about 2,000 units) was charged in a column having a diameter of 1.5 cm. Warm water was circulated to increase the internal temperature to 50°C and 0.2 mole of an N-acetyl-DL-2-aminobutyric acid solution (pH=7.0) was continuously fed from the top of the column at a flow rate of 5 ml/hour. Even after conducting the continuous reaction for about 500 hours, no reduction in the enzyme activity was observed and a conversion of about 100% was obtained, which were surprisingly excellent results.

In the same manner as in Example 1, the reactant solution was treated with activated carbon and an ion exchange resin, and thus L-2-aminobutyric acid having an optical purity of 99% or more was obtained.

50 parts of a 0.1 M phosphoric acid buffer solution (pH=8.0). After about 3 hours, the wet carrier was separated, washed several times with water, and finally freezedried. The enzyme activity of the immobilized enzyme to N-acetyl-DL-2-aminobutyric acid was about 700 units/g.

Continuous Production of L-2-Aminobutyric Acid

Under the same continuous reaction conditions as described in the Example 3, the continuous reaction was conducted using 1 g of the above immobilized enzyme (about 700 units) for about 300 hours, and, as a result, a conversion of about 70% was obtained.

By treating the thus obtained reactant solution with activated carbon and an ion exchange resin in the same manner as described in Example 1, L-2-aminobutyric acid having an optical purity of 98.5% or more was obtained.

EXAMPLES 5 TO 8

In the same manner as described in Example 3, an immobilized acylase was prepared using anion exchange resins containing various quaternized pyridine rings in the resin molecule as indicated in Table 1 below. With the resulting immobilized acylase, N-acyl-DL-2-aminobutyric acid was subjected to continuous optical resolution in the same manner as described in Example 3 to produce L-2-aminobutyric acid.

The composition of the carrier, the reaction conditions used and the results obtained are shown in Table 1 below.

Table 1

| Example | Process for Production of Exchange Resin | | | REACTION CONDITIONS Properties*[1] | | Adsorption Condition, Weight Ratio Carrier/ Acylase | Activity*[2] of Immobilized Enzyme (units/g) |
|---|---|---|---|---|---|---|---|
| | Kind and Composition (mole %) | Polymerization Method | Quaternizing Agent | Anion Exchange Capacity (mmol/g) | Degree of Swelling (vol/g) | | |
| 5 | Methyl Methacrylate/ Pyridine/Divinyl Benzene (23: 76: 1) | Radical | $CH_3Br$ | 3.9 | 20 | 1/1 | 2300 |
| 6 | " | " | " | " | " | 1/0.5 | 1500 |
| 7 | 2-Vinyl Pyridine/ Ethylene Glycol Dimethacrylate (95:5) | " | $CH_3Cl$ | 4.9 | 15 | 1/1 | 1700 |
| 8 | 2-Methyl-5-vinyl Pyridine/Divinyl Benzene (95:5) | " | " | " | 10 | 1/1 | 1500 |

Notes:
*[1] 0.5 g of a dry ion exchange resin was immersed in 50 ml of a 0.1 M phosphoric acid buffer soltuon (pH=8.0) and charged in a column having a diameter of 1.0 cm and a height of 50 cm, and the Bet volume under equilibrium swelling was measured and indicated as ml/g dry ion exchange resin.
*[2] Activity unit where N-acetyl-DL-2-aminobutyric acid was used as a substrate.

| | Reaction Conditions | | Reaction Results (Conversion) | | |
|---|---|---|---|---|---|
| Example | Immobilized Enzyme (g) | Flow Rate (ml/hr) | After 300 Hours (%) | After 500 Hours (%) | after 700 Hours (%) |
| 5 | 1 | 5 | 100 | 100 | 90 |
| 6 | 1 | 5 | 100 | 80 | — |
| 7 | 1 | 5 | 100 | 70 | — |
| 8 | 1 | 5 | 95 | 70 | — |

EXAMPLE 4

Immobilization of Acylase with DEAE-Sephadex 25 parts of DEAE-Sephadex (trademark manufactured by Pharmacia Fine Chemical Co., Ltd.) was placed in 50 parts of a 0.1 M phosphoric acid buffer solution having a pH of 8.0 for 24 hours and filtered. Thus a wet carrier was obtained. The wet carrier was added with stirring at room temperature to an enzyme solution produced by dissolving 0.5 parts of a commercially available fungal acylase (about 10,000 units/g) in Production of (+)-2-Amino-1-butanol

EXAMPLE 9

1.8 g of L-2-aminobutyric acid as obtained in Example 5 was dispersed in 30 ml of ethanol and dry hydrogen chloride gas was bubbled through the dispersion until the L-2-aminobutyric acid was completely dissolved to form a homogeneous solution, and then the solution was refluxed for 4 hours. After cooling, the ethanol was removed under reduced pressure. The crystals obtained were dissolved by adding aqueous ammonia while cooling and then extracted with diethyl ether. The extract was dried with magnesium sulfate and distilled under reduced pressure, and thus 2.0 g of a L-2-aminobutyric acid ethyl ester fraction (b.p. 66°–67°C/18 mm Hg) was obtained. The yield was 90%. $(\alpha)_D^{27} = +17.8° \pm 1°$ (C = 5.6, ethanol).

1.5 g of the thus obtained L-2-aminobutyric acid ethyl ester was dissolved in 20 ml of ethanol. To the solution was added 3 g of Raney nickel which was digested at 50° to 60°C for 50 to 60 minutes to make it sponge-like. The mixture was stirred under the conditions of a temperature of 50° to 60°C and a hydrogen pressure of 10 Kg/cm² for 16 hours. After the reaction was completed, the mixture was cooled and hydrogen was removed. Thereafter, the reaction mixture was diluted by adding 20 to 30 ml of ethanol and the Raney nickel was removed by filtration. The filtrate was concentrated and distilled under reduced pressure, and thus 0.8 g of a (+)-2-amino-1-butanol fraction (b.p. 89°C/18 to 19 mm Hg) was obtained.

The yield was 78.4% based upon the ester. $(\alpha)_D^{29} = +9.5° \pm 0.5°$ (C=10.6, methanol) $(\alpha)_D^{33} = +9.84 \pm 0.05°$.

The optical purity was about 100% on the basis of the value: $(\alpha)_D^{25} = +9.8°$ as described in Merck Index (7th Edition).

EXAMPLE 10

1.5 g of L-2-aminobutyric acid was dispersed in 30 ml of iso-propanol and a dry hydrogen chloride gas was bubbled through the dispersion until the L-2-aminobutyric acid was completely dissolved to form a homogeneous solution, and then the solution was refluxed for 16 to 17 hours. After cooling, the iso-propanol was removed under reduced pressure. The crystals obtained were dissolved by adding aqueous ammonia while cooling and then extracted with diethyl ether. The extract was dried with magnesium sulfate and distilled under reduced pressure, and 1.9 g of an L-2-aminobutyric acid iso-propyl ester fraction (b.p. 68° to 69°C/15 mmHg) was obtained. The yield was 90.5%. 1.9 g of the thus obtained L-2-aminobutyric acid iso-propyl ester was dissolved in 30 ml of iso-propanol. To the solution was added 0.57 g of platinum oxide. The mixture was stirred under the conditions of a temperature of 50° to 70°C and a hydrogen pressure of 10 Kg/cm² for 15 to 16 hours.

After the reaction was completed, the mixture was cooled and the hydrogen was removed. Thereafter, the reaction mixture was diluted with 20 to 30 ml of iso-propanol. The platinum oxide was filtered off. The filtrate was concentrated and distilled under reduced pressure, and thus 0.7 g of a (+)-2-amino-1-butanol fraction (b.p. 93.5°C/24 mm Hg) was obtained. The yield was 60.3% based upon the ester. $(\alpha)_D^{33} = +9.89° \pm 0.05°$. The optical purity was about 100% on the basis of the value $(\alpha)_D^{25} = +9.8°$.

EXAMPLES 11 TO 14

L-2-aminobutyric acid produced in the same manner as in Example 9 was subjected to a catalytic reduction under the conditions as indicated in Table 2 to produce (+)-2-amino-1-butanol. The kind of reducing catalyst and reducing conditions used and the results obtained are shown in Table 2.

Table 2

| Example Number | Reducing Catalyst | Amount of Catalyst (% by wt) | Temperature (°C) | Hydrogen Pressure (Kg/cm²) | Reaction Period (hrs.) | Yield of (+)-2-Amino-1-butanol (%) | Optical Purity of (+)-Amino-* 1-butanol Obtained (%) |
|---|---|---|---|---|---|---|---|
| 11 | Raney Nickel | 100 | 40 to 60 | 30 | 16 | 81.0 | 100 |
| 12 | Raney Nickel | 50 | 60 to 70 | 50 to 70 | 16 | 72.5 | 98 |
| 13 | Platinum Oxide | 10 | 60 to 70 | 50 | 16 | 65.0 | 98 |
| Comparison Example | Raney Nickel | 30 | 80 to 100 | 100 to 120 | 16 | 23.0 | 85 |

Note:
*The optical purity of (+)-2-amino-1-butanol is based upon the value:
$(\alpha)_D^{25} = +9.8°$ as described in Merck Index (7th Edition).

EXAMPLE 15

An aqueous solution containing the N-acetyl-D-aminobutyric acid and a small the of L-2-aminobutyric acid which remained unadsorbed on the ion-exchange resin in Example 2 was evaporated under reduced pressure to remove water and acetic acid to obtain crystals having a water content of 0.2, 1.0 and 2.0% by weight, respectively. The resulting crystals were heated at 140°C for 3 hours for racemization and the results obtained are shown below.

| Water Contents of Crystals (% by wt.) | Racemization Yield | |
|---|---|---|
| | N-Acyl-D-amino-butyric Acid (%) | L-2-Aminobutyric Acid (%) |
| 0.2 | 100 | 0 |
| 1.0 | 70 | 0 |
| 2.0 | 20 | 0 |

In the same manner as described above, crystals having a water content of 20% by weight were heated under the same conditions as used above. Racemization of N-acetyl-D-aminobutyric acid was partially observed but most of the crystals were found to be decomposed into DL-2-aminobutyric acid.

EXAMPLE 16

In the same manner as described in Example 15, the water content of N-acetyl-D-aminobutyric acid was reduced to 30% by weight. To the resulting crystals was added xylene in an amount 5 times the weight of the crystals followed by heating to azeotropically distil off water. The mixture was further heated at the boiling point of xylene for 2 hours and then cooled to obtain crystals.

The N-acetyl-D-aminobutyric acid contained in the starting crystals was found to be 100% racemized.

While the invention has been described in detail and with reference to specific embodiments thereof, it will be apparent to one skilled in the art that various changes and modifications can be made therein without departing from the spirit and scope thereof.

What is claimed is:

1. A process for producing (+)-2-amino-1-butanol which comprises
   1. optically resolving an N-acyl-DL-2-aminobutyric acid in an aqueous solution using the action of an acylase to obtain (A) an aqueous solution predominantly comprising L-2-aminobutyric acid and a small amount of an N-acyl-D-2-aminobutyric acid and (B) an aqueous solution predominantly comprising an N-acyl-D-2-aminobutyric acid and a small amount of L-2-aminobutyric acid,
   2. isolating crystalline L-2-aminobutyric acid from said solution (A) and to obtain a solution (C) from which said L-2-aminobutyric acid has been isolated,
   3. esterifying said crystalline L-2-aminobutyric acid to form an L-2-aminobutyric acid ester,
   4. reducing the L-2-aminobutyric acid ester to form (+)-2-amino-1-butanol, said reducing occurring in the presence of Raney nickel in an amount higher than about 50% by weight or platinum in an amount higher than about 10% by weight based on the amount of said L-2-aminobutyric acid ester at temperatures of ambient temperature to about 70°C and a hydrogen pressure below about 70 Kg/cm$^2$
   5. combining said solution (B) and said solution (C) to form a solution (D),
   6. crystallizing said N-acyl-D-2-aminobutyric acid from said solution (D) to obtain crystals comprising predominantly said N-acyl-D-2-aminobutyric acid and a small amount of said L-2-aminobutyric acid, and
   7. racemizing said crystals comprising predominantly said N-acyl-D-2-aminobutyric acid to obtain an N-acyl-DL-2-aminobutyric acid for recycle to step (1).

2. The process according to claim 1, wherein said acylase is immobilized on a carrier.

3. The process according to claim 2, wherein said carrier is an anion exchange resin containing quaternized pyridine rings in the molecule.

4. The process according to claim 3, wherein the anion exchange resin has an anion exchange capacity of about 2.0 to 5.0 millimole equivalent/g and a degree of swelling of about 2.0 to 50.0 ml/g in a 0.1 M phosphoric acid buffer solution having a pH of 8.0.

5. The process according to claim 1, wherein said resolving is at a concentration of about 0.05 to 1 mole per liter of the N-acyl-DL-2-aminobutyric acid at a temperature of about 30° to 70°C at a pH of from about 5 to 8.5 using an aqueous solution of a fungal acylase having a concentration of about 0.05 to 1 mol % in an amount of about 40 to 4,000 units per g of said N-acyl-DL-aminobutyric acid for less than about 100 hours.

6. The process according to claim 1, wherein said resolving is at a temperature of about 50°C at a pH of from about 5 to 8.5 by passing an aqueous solution of said N-acyl-DL-2-aminobutyric acid having a concentration of about 0.05 to 1 mol % at a space velocity of about 0.05 to 10 hr$^{-1}$, through a column packed with an anion exchange resin having adsorbed thereon an aqueous solution of an acylase in an amount of about 0.5 to 1.0 part by weight per 1 part of said resin.

7. The process according to claim 1, wherein the resolving is continuously carried out using an acylase immobilized on a carrier.

8. The process according to claim 1, wherein said racemizing is at about 110° to 170°C for about 5 minutes to 24 hours while maintaining the water content of said crystals below about 1% by weight.

9. The process according to claim 8, wherein said racemizing is at 140° to 160°C.

10. The process according to claim 8, wherein said water content is below 0.5% by weight.

11. The process according to claim 1, wherein said racemizing is in the presence of an inert solvent.

12. The process according to claim 11, wherein said inert solvent is selected from the group consisting of a saturated aliphatic or alicyclic hydrocarbon, an aromatic hydrocarbon, a straight chain ether, a cyclic ether, an alkyl mononitrile, an alkyl dinitrile and a carboxylic acid ester.

13. The process according to claim 11, wherein said solvent is capable of forming an azeotropic mixture with water.

* * * * *